United States Patent
Goto et al.

(10) Patent No.: US 10,180,412 B2
(45) Date of Patent: Jan. 15, 2019

(54) SUPERCRITICAL FLUID DEVICE

(71) Applicant: Shimadzu Corporation, Kyoto (JP)

(72) Inventors: Hiroomi Goto, Nara (JP); Risa Kajiyama, Moriyama (JP); Takahiro Mori, Kyoto (JP)

(73) Assignee: Shimadzu Corporation, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 15/557,769

(22) PCT Filed: Mar. 19, 2015

(86) PCT No.: PCT/JP2015/058243
§ 371 (c)(1),
(2) Date: Sep. 12, 2017

(87) PCT Pub. No.: WO2016/147379
PCT Pub. Date: Sep. 22, 2016

(65) Prior Publication Data
US 2018/0074026 A1    Mar. 15, 2018

(51) Int. Cl.
*G01N 30/30* (2006.01)
*F16L 53/38* (2018.01)
*B01D 15/40* (2006.01)

(52) U.S. Cl.
CPC ............ *G01N 30/30* (2013.01); *F16L 53/38* (2018.01); *B01D 15/40* (2013.01);
(Continued)

(58) Field of Classification Search
CPC .......... G01N 30/30; G01N 2030/3038; G01N 2030/3053; G01N 2030/3061; B01D 15/161; B01D 15/40; F16L 53/38
See application file for complete search history.

(56) References Cited

U.S. PATENT DOCUMENTS 4,484,061 A * 11/1984 Zelinka ................. G01N 30/30
137/341
7,964,029 B2 * 6/2011 Fogelman .......... B01D 11/0203
96/155
(Continued)

FOREIGN PATENT DOCUMENTS

JP    2002-071534 A    3/2002
JP    2009-544042 A    12/2009
(Continued)

*Primary Examiner* — Justin N Olamit
(74) *Attorney, Agent, or Firm* — Muir Patent Law, PLLC

(57) ABSTRACT

Provided is a supercritical fluid device equipped with a back pressure regulator for creating a pressurized state in which a mobile phase in a separation/extraction unit of an analysis flow passage is kept in a supercritical fluid state. One end of a pipe is connected to an outlet side of the back pressure regulator, and the other end of the pipe is open to the atmosphere. A heating unit is provided on the pipe, and the heating unit includes a plurality of electrically independent heaters arranged on mutually different portions of the pile along the pipe. A power supply controller is connected to the heaters, and the power supply controller is configured to supply heating power to one or more heaters selected among the plurality of heaters, but to not supply heating power to the other heaters.

5 Claims, 5 Drawing Sheets

(52) U.S. Cl.
CPC ........ *G01N 2030/3007* (2013.01); *G01N 2030/3038* (2013.01); *G01N 2030/3053* (2013.01)

(56) References Cited

U.S. PATENT DOCUMENTS

| | | | |
|---|---|---|---|
| 8,965,187 B2* | 2/2015 | Borgmeier | H05B 3/46 |
| | | | 392/480 |
| 2002/0139752 A1 | 10/2002 | Berger et al. | |
| 2008/0010956 A1 | 1/2008 | Fogelman et al. | |
| 2011/0094606 A1 | 4/2011 | Kanomata et al. | |

FOREIGN PATENT DOCUMENTS

| | | |
|---|---|---|
| JP | 2011-118880 A | 6/2016 |
| WO | WO 2014/083839 A1 | 6/2014 |

\* cited by examiner (a) Flow rate: 20 ml/min (b) Flow rate: 50 ml/min (c) Flow rate: 100 ml/min (c) Flow rate: 150 ml/min (a) $CO_2$ : 150 ml/min (Normal maximum feed rate of preparative SFC)
    State of freezing at the time of the liquid feed (b) State that freezing is prevented by voltage application

SUPERCRITICAL FLUID DEVICE

TECHNICAL FIELD

The present application relates to a supercritical fluid device including a supercritical fluid chromatograph (SFC) and a supercritical fluid extractor (SFE).

BACKGROUND ART

In supercritical fluid chromatography, when a supercritical fluid of 10 MPa or more as a mobile phase, which is, for example, liquefied carbon dioxide ($CO_2$) or a fluid in which an organic solvent as a modifier is added to liquefied carbon dioxide, is vaporized after being reduced to atmospheric pressure after passing through a back pressure regulator (BPR), the temperature drastically decreases due to the adiabatic expansion and the vaporization heat. At that time, carbon dioxide turns into dry ice, causing freezing or clogging of a pipe. To prevent this, it is practiced to heat a back pressure regulator or a pipe arranged on a downstream side of the back pressure regulator with respect to the flow of the mobile phase.

In order to prevent an outlet flow passage opening of the back pressure regulator from being clogged or broken by dry ice, it is known that a back pressure regulator itself is heated with a heater (see Patent Document 1). In Patent Document 1, there is no description that the outlet side pipe of the back pressure regulator is heated.

There is a case in which a pipe connected to an outlet flow passage of a back pressure regulator is wound around a heat exchange block provided with a cartridge heater to heat the vaporized fluid flowing through the pipe to thereby prevent freezing of the pipe (see Patent Document 2). In this case, the entire pipe wound around the heat exchange block is constantly heated.

Further, there is a case in which a cartridge heater and a trim heater are provided between a back pressure regulator and a transfer pipe to a fraction collector to completely evaporate liquefied carbon dioxide portion of the discharged fluid to thereby prevent ice formation on the outside of the transfer pipe (see Patent Document 3). Also in this example, the portion to be heated by the cartridge heater and the trim heater is fixed.

PRIOR ART

Patent Document

Patent Document 1: U.S. Pat. No. 5,224,510
Patent Document 2: U.S. Patent Application Publication Specification No. 2011/0094604
Patent Document 3: Japanese Unexamined Patent Application Publication No. 2002-71534

SUMMARY OF THE INVENTION

Problems to be Solved by the Invention

Even in a supercritical fluid chromatograph device and a supercritical fluid extractor, when separated or extracted sample components are detected with a detector or collected in a container, a mobile phase is not released directly from an outlet of a back pressure regulator but is often released by way of a pipe.

Since residual pressure due to pipe resistance is applied to the mobile phase in the pipe, liquefied carbon dioxide in the mobile phase does not immediately vaporize after passing through the back pressure regulator, but vaporizes when the pressure loss from the pipe outlet becomes lower than about 5 MPa. In other words, the position where liquefied carbon dioxide is vaporized in the pipe varies depending on parameters such as the inner diameter of the pipe to be used, the flow rate, and the modifier mixing rate (corresponding to the carbon dioxide feeding amount). This means that heating of a fixed portion as described in the above-mentioned prior art document is not appropriate depending on parameters or that entire heating causes deteriorated thermal efficiency.

For example, under the conditions that vaporization occurs at a location further downstream from a heating mechanism attached to a back pressure regulator or a heating mechanism arranged at a fixed position downstream of the back pressure regulator, in order to prevent freezing at that location, an amount of heat for compensating for the temperature drop due to the adiabatic expansion and the vaporization heat of carbon dioxide should be given to the mobile phase including liquefied carbon dioxide on the upstream side of the location where the possible freezing occurs. This results in a markedly raised temperature of the mobile phase at the location of the heating mechanism. For example, in preparative supercritical fluid chromatography, there exist many samples to be injected which are thermally decomposed, and therefore excessive temperature rise causes disappearance or denaturalization of the sample.

On the other hand, for example, in cases where vaporization of liquefied carbon dioxide occurs at a location upstream of a heating mechanism arranged at a fixed position downstream of the back pressure regulator, even if how much heat is applied to the mobile phase with the heating mechanism at that position, freezing of the pipe cannot be prevented.

Such a problem occurs not only in preparative a supercritical fluid chromatograph but also in a supercritical fluid chromatograph and a supercritical fluid extractor which detect separated components.

The present invention aims to efficiently prevent occurrence of freezing or clogging of a pipe arranged on a downstream side of a back pressure regulator.

Means for Solving the Problems

In the present invention, it is not configured to always heat a specific portion but enable heating of an appropriate portion depending on parameters such as a pipe inner diameter and a flow rate of liquefied carbon dioxide.

A supercritical fluid device according to the present invention is equipped with a supercritical fluid analysis unit, the supercritical fluid analysis unit including an analysis flow passage equipped with a separation/extraction unit configured to separate or extract a sample component, a fluid feeder equipped with a pump and configured to supply a mobile phase which becomes a supercritical fluid to the analysis flow passage arranged on an upstream side of the separation/extraction unit, and a back pressure regulator arranged on a downstream side of the separation/extraction unit with respect to a flow of the mobile phase and configured to create a pressurized state in which the mobile phase in the separation/extraction unit is kept in a supercritical fluid state.

The supercritical fluid device according to the present invention is equipped with a pipe having one end connected to an outlet side of the back pressure regulator of the supercritical fluid analysis unit and the other end opened to atmosphere, a heating unit equipped with a plurality of electrically independent heaters arranged on mutually different portions of the pipe along the pipe, and a power supply controller connected to the heaters and configured to supply heating power source to one or a plurality of heaters selected from the plurality of heaters but to not supply heating power to the other heaters.

Effects of the Invention

In the present invention, since any part of the pipe connected to the outlet side of the back pressure regulator can be selectively heated, the pipe can be heated with one or a plurality of heaters at locations most suitable for preventing freezing of the pipe. As a result, it is possible to prevent a sample from being decomposed or disappeared by not giving excessive heat to a mobile phase upstream of a frozen portion of the pipe, and also possible to eliminate a problem that freezing cannot be prevented by heating the downstream of the freezing portion of the pipe.

Further, since necessary portions can be efficiently heated, unnecessary flow passages for merely conveying heat capacity can be reduced, and since a dead volume can be reduced, spreading of the peak separated by a column can be suppressed.

EMBODIMENTS FOR CARRYING OUT THE INVENTION

Figure 1:
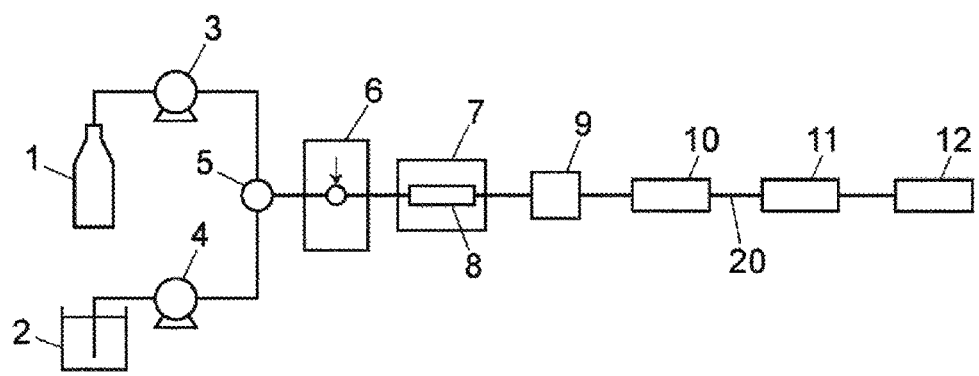
FIG. 1 is a block diagram showing a preparative supercritical fluid chromatograph according to one embodiment.

When a pipe is connected to the outlet side of a back pressure regulator, although the inner diameter of the pipe is known, the position where freezing occurs cannot be determined only by the inner diameter, and varies depending on analysis conditions such as a mobile phase flow rate and a modifier mixing rate. Therefore, it is preferable to be able to prevent occurrence of freezing at any position of the pipe. For this reason, in one embodiment, a heater is arranged substantially over the entire length of the pipe. Since it may sometimes be impossible to arrange a heater at an end portion of a pipe due to other parts connected thereto, the wording "substantially over the entire length" means to place a heater over the entire length of the pipe except for a portion, such as an end portion of a pipe, where a heater cannot be arranged.

Although the type of the heater is not particularly limited, a film heater is preferably used as a heater suitable for arranging at a plurality of portions along the pipe. In that case, a plurality of segmented film heaters is used by winding around a pipe. In the film heater, it is unnecessary to provide a plurality of heating components like a heating mechanism composed of a cartridge heater and a heat exchange block, so that the heater portion can be made compact.

All of the plurality of segmented heaters are not used for heating by being simultaneously energized, and one or a plurality of heaters arranged at positions where freezing is to be prevented are selectively used. For this reason, in one embodiment, the power supply controller has a switch and a control circuit for setting energization per heater. A frozen portion of a pipe is determined by parameters such as a pipe inner diameter, a flow rate, and a modifier mixing rate. Therefore, first, in a state in which no heater is energized, a supercritical fluid device is activated under operating parameters, and a point where freezing actually occurs is specified. Thereafter, in operation, the operator manipulates the switch so as to energize a heater arranged at the freezing portion or a plurality of heaters including the heater and its anteroposterior heaters.

Furthermore, even when energizing a plurality of heaters, it is not necessary that the amount of energization to all heaters to be energized should be equally set. Rather, it is preferable to configure such that the amount of energization to heaters to be used can be individually adjusted so that, for example, the amount of energization to a heater at a location where freezing is most likely to occur can be increased and the amount of energization to its adjacent heaters can be reduced. Therefore, in one embodiment, the switch and the control circuit are configured such that the amount of energization to a heater is feedback-controlled so that the temperature of the pipe becomes a predetermined temperature. For the feedback control, a temperature sensor may be provided for each heater to perform feedback control so that the detected temperature of the temperature sensor becomes a predetermined temperature. Further, when using a film heater as the heater, even if a temperature sensor is not provided, the temperature can be detected by the resistance value of the film heater. Therefore, feedback control can be performed so that the resistance value of the heater becomes a predetermined resistance value.

Instead of manipulating switches by an operator, it may be configured so that the device is provided with an input unit for inputting information on energization for each heater, such as which heater to use, and a control unit for setting energization for each heater based on input information from the input unit.

Since it is possible to obtain in advance the relationship between parameters including the pipe inner diameter and analysis conditions of the supercritical fluid device and the freezing portion of the pipe, such a pre-determined relationship can be retained. Therefore, in one embodiment, the power supply controller is equipped with a positional information holder which holds positional information indicating the freezing portion of the pipe with respect to multiple parameters of the supercritical fluid analysis unit including the pipe inner diameter and the liquefied carbon dioxide flow rate in a mobile phase, and an input unit for inputting parameters during the operation of the supercritical fluid device, and a control unit that selectively energizes heaters arranged at the freezing portions of the tube based on the parameter input from the input unit and the positional information held in the positional information holder.

Next, a configuration of one embodiment of a preparative supercritical fluid chromatograph as a supercritical fluid device according to one embodiment will be described with reference to FIG. 1.

In a supercritical fluid chromatograph, in general, liquefied carbon dioxide in which a supercritical state can be obtained at relatively low temperature and low pressure is used, and an organic solvent as a modifier for increasing solubility of a sample to be measured is mixed into liquefied carbon dioxide. An example of a modifier is methanol. A mixture in which a modifier is mixed into liquefied carbon dioxide is served as a mobile phase. Therefore, liquefied carbon dioxide obtained from a carbon dioxide cylinder 1 is sent by a carbon dioxide pump 3, and a modifier 2 is sent by a modifier pump 4. The liquefied carbon dioxide and the modifier are mixed in a mixer 5 to be served as a mobile phase.

The mobile phase in which the sample was injected by an autosampler 6 passes through a column 8 arranged in a column oven 7, so that the sample is temporally separated. The temporally separated sample is detected by a detector 9. The detector 9 is, for example, an ultraviolet (UV) detector.

The pressure of the mobile phase in the flow passage downstream of the pumps 3 and 4 is kept constant at about 10 MPa or more by a pressure control valve as a back pressure regulator 10. The outlet side of the back pressure regulator 10 is connected to a fraction collector 12 via a pipe 20, and the separated sample components are collected by the fraction collector 12. After passing through the back pressure regulator 10, the mobile phase is depressurized to the atmospheric pressure, and liquefied carbon dioxide in the mobile phase becomes gas when the pressure decreases to about 5 MPa which is the threshold value of carbon dioxide vaporization.

In order to prevent the passage of the pipe 20 from freezing and clogging due to the vaporization heat, the pipe 20 on the outlet side of the pressure control valve 10 is provided with a heating unit 11 of this embodiment.

In a preparative supercritical fluid chromatograph, a gas-liquid separator may sometimes be installed in front of the fraction collector 12. In this case, the fraction collector 12 is described as including such a gas-liquid separator.

The heating unit 11 will be described. In a device using a mobile phase of a large flow rate (about 10 to 150 ml/min), such as a preparative supercritical fluid chromatograph, since parameters including a pipe inner diameter and a liquefied carbon dioxide flow rate may differ for each user or preparative conditions as described above, the vaporization point of liquefied carbon dioxide varies depending on those parameters. If the heater of the heating unit 11 is provided only at a specific position, freezing may occur downstream of that position. In such a case, since the heater of the heating unit 11 needs to give a more amount of heat to the mobile phase than heating at the freezing portion, decomposition and/or denaturation of the sample due to the excessive mobile phase temperature rise becomes a problem.

Figure 2:
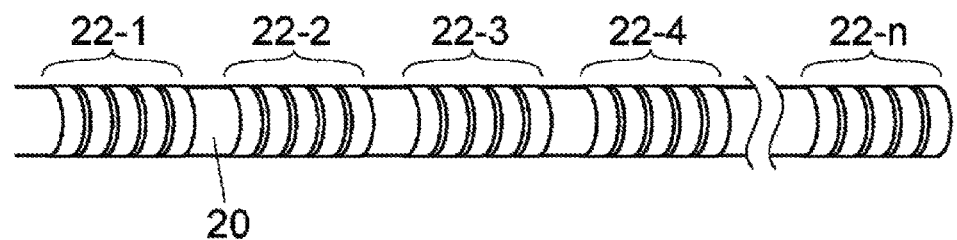
FIG. 2 is a schematic perspective view showing a pipe and a film heater wound around the pipe according to one embodiment.

In this embodiment, in order to solve the problem, the heating unit 11 is provided over substantially the entire pipe 20 from the back pressure regulator 10 to the fraction collector 12. As shown in FIG. 2, the heating unit 11 is formed by winding film heaters 22-1 to 22-n divided into a plurality of segments on the pipe 20, so that the pipe 20 is a pipe with a heating function. The film heaters 22-1 to 22-n are wound over almost the entire length of the pipe 20 along the pipe 20, and are arranged in different parts of the pipe 20. The respective film heaters 22-1 to 22-n are electrically independent from each other, that is, they are connected to a power source so that they can be energized independently.

In a preparative supercritical fluid chromatograph, it is common that a pipe having an inner diameter of 0.5 to 1.0 mm is connected to the outlet side of a back pressure regulator. In this embodiment, the pipe 20 is a stainless steel tube having an inner diameter of 1.0 mm, an outer shape of ($\frac{1}{16}$) inches, and a length of 30 cm to 2 m. The film heaters 22-1 to 22-n are, for example, commercially available polyimide heaters. Each of the segmented film heaters 22-1 to 22-n has a width of 1 to 10 cm, for example, a width of about 5 cm, and is spaced apart from each other by 1 mm to 1 cm.

During the preparation of the preparative supercritical fluid chromatograph, necessary segments of the film heaters 22-1 to 22-n are energized so that there is no part below 0° C. anywhere on the pipe 20. The temperature of the pipe 20 wound by the heater among the film heaters 22-1 to 22-n to be energized may be any temperature as long as it does not become 0° C. or below, but it is appropriate to control the energization so that the temperature becomes about 10 to 30° C. The energization to the film heaters 22-1 to 22-n can be feedback-controlled based on the temperature measurement. For example, it may be configured such that a temperature sensor such as a thermistor is attached to the pipe 20 for each of the film heaters 22-1 to 22-n and feedback control is performed so that the temperature detected by each sensor becomes a predetermined temperature. Alternatively, it may be configured such that the resistance values of the film heaters 22-1 to 22-n are read and feedback control is performed based on a value obtained by converting the read resistance values into measured temperatures.

Figure 3:
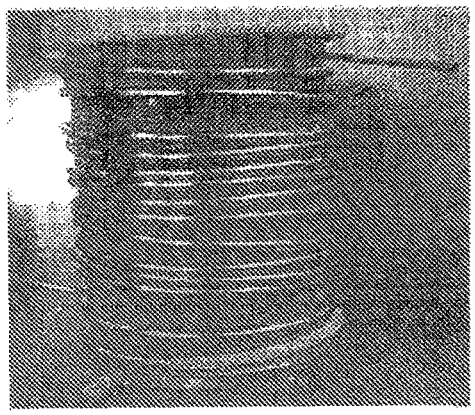
FIG. 3 is an image showing how a pipe is frozen when a flow rate of carbon dioxide as a mobile phase is changed.
Figure 3:
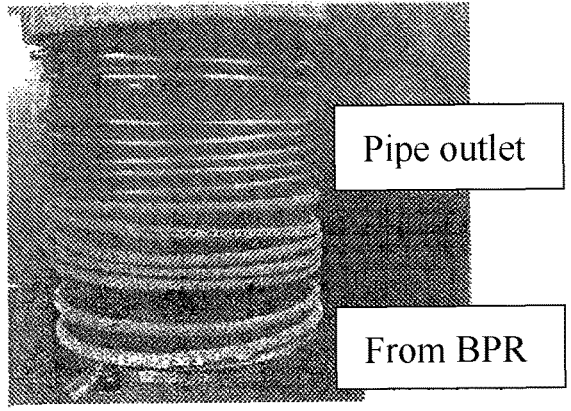
Figure 3:
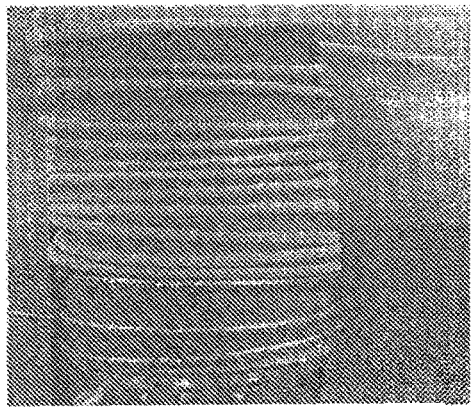
Figure 3:
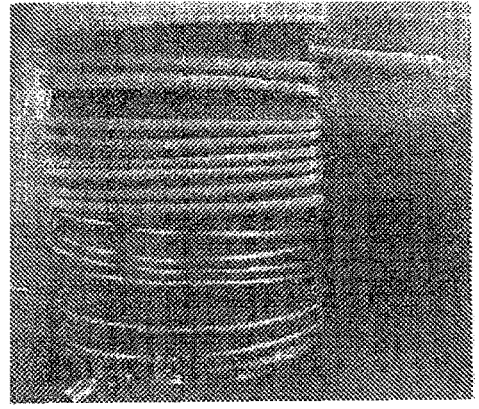

The position of the pipe 20 where freezing occurs varies depending on parameters including the inner diameter of the pipe 20 and the mobile phase difference flow rate. A specific example is shown in FIG. 3. FIG. 3 shows states of pipe freezing when changing a flow rate of a mobile phase in a state in which a pipe is connected immediately after a back pressure regulator in a supercritical fluid chromatograph and no heater is provided for the pipe, and only liquefied carbon dioxide is set as a mobile phase. In each figure of (A) to (D), the lower side is the back pressure regulator side and the upper side is the pipe outlet side. The pipe had an inner diameter of 0.8 mm and a length of 2 m, and was wound around a cylindrical block (aluminum material) having a diameter of 40 mm. At a flow rate of 20 ml/min (A), the pipe was frozen up to the middle of the first lap immediately behind the back pressure regulator, i.e., between approximately 0 and 10 cm. As the flow rate increased, the frozen position was between approximately 0 an 1 m at 50 ml/min (B), between approximately 0.5 and 2 m at 100 ml/min (C), between approximately 1 to 2 m at 150 ml/min (D). In other words, the freezing position is moving toward the pipe outlet. This means that the pipe resistance becomes larger as the flow rate increases and therefore the portion where the pressure drop from the pipe outlet is below about 5 MPa which is the threshold of carbon dioxide vaporization (vaporization point) of carbon dioxide vaporization is close to the pipe outlet.

In the example of FIG. 3, a pipe having an inner diameter of 0.8 mm was used. However, the vaporization point varies depending on the pipe inner diameter. For example, in a pipe having an inner diameter of 1.0 mm, liquefied carbon dioxide will be vaporized on the upstream side than the results shown in FIG. 3. In a pipe having an inner diameter of 0.5 mm, the vaporization point will be on the downstream side than the results shown in FIG. 3.

As described above, when parameters such as a pipe inner diameter and a liquefied carbon dioxide flow rate are determined, the vaporization point, that is, the freezing position will, be determined. If the relationships between such parameters and freezing positions are obtained in advance through experiments, when a plurality of heaters are arranged along the pipe according to an embodiment of the present invention, it is possible to operate such that one or a plurality of heaters including heaters corresponding to the freezing positions are energized. As described in the embodiment shown in FIGS. 6 to 8 which will be described later, heaters to be heated by energization may be set manually or may be set automatically by inputting data.

Figure 4:
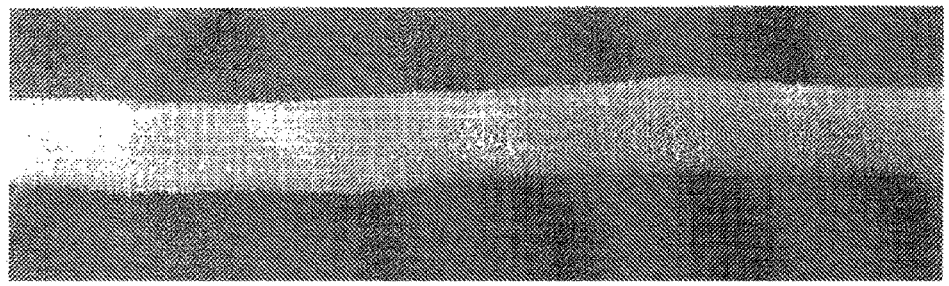
FIG. 4 is an image showing a frozen state (A) and a frozing prevented state (B) in a pipe in a supercritical fluid chromatograph of one embodiment.
Figure 4:
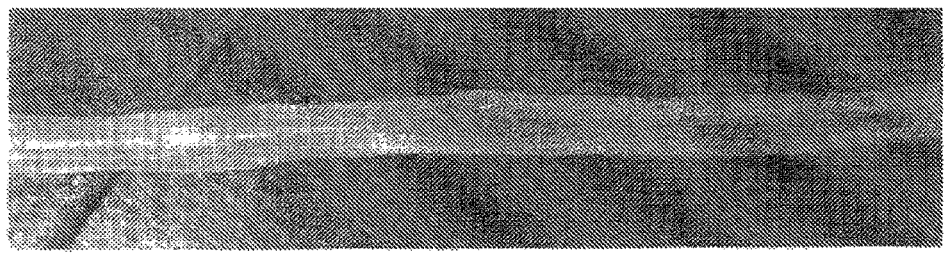

FIG. 4 shows a frozen state and a freezing prevented state in a pipe in a supercritical fluid chromatograph of one example. The pipe was a pipe having a heating function with an inner diameter of 0.8 mm and a length of 50 cm. A film heater was wound around the pipe, and the outer periphery thereof was covered by polytetrafluoroethylene for burn prevention. This pipe was attached to the outlet side of the back pressure regulator and liquefied carbon dioxide was sent as a mobile phase at a flow rate of 150 ml/min and experiments were carried out. The liquefied carbon dioxide flow rate of 150 ml/min is the maximum feed volume of a typical preparative supercritical fluid chromatograph. (A) shows a case in which no heater at any positions was energized. The picture shows the frozen portion which is a part of the 50 cm pipe. Next, by energizing the heater at the frozen portion to heat, the frozen disappeared as shown in (B). From the above, it is understood that anti-freeze can be performed by partially heating the pipe.

Figure 5:
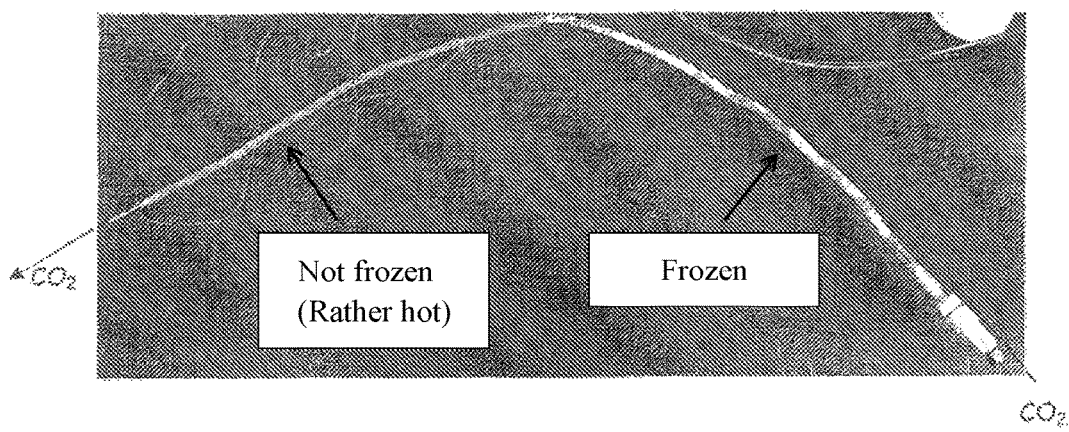
FIG. 5 is an image showing a result of heating by energizing all heaters of a 50 cm pipe with a heating function in a supercritical fluid chromatograph according to one embodiment.

FIG. 5 shows the result in the case where all the heaters of the 50 cm pipe having a heating function were energized to thermally control the entire pipe uniformly. According to the heating conditions at this time, since the liquefied carbon dioxide was vaporized near the inlet of the pipe, the freezing near the pipe outlet was prevented due to heating, rather it became hot, whereas heating near the pipe inlet was insufficient and therefore the portion near the pipe inlet was frozen. Increasing the amount of energization to the entire heater prevents freezing of the entire pipe, but causes further increase in the temperature near the pipe outlet.

From this result as well, it is understood that it is preferable that heating control be performed not by uniformly heating the entire pipe but by dividing the heater into a plurality of segments in the pipe longitudinal direction and independently controlling the segments.

Figure 6:
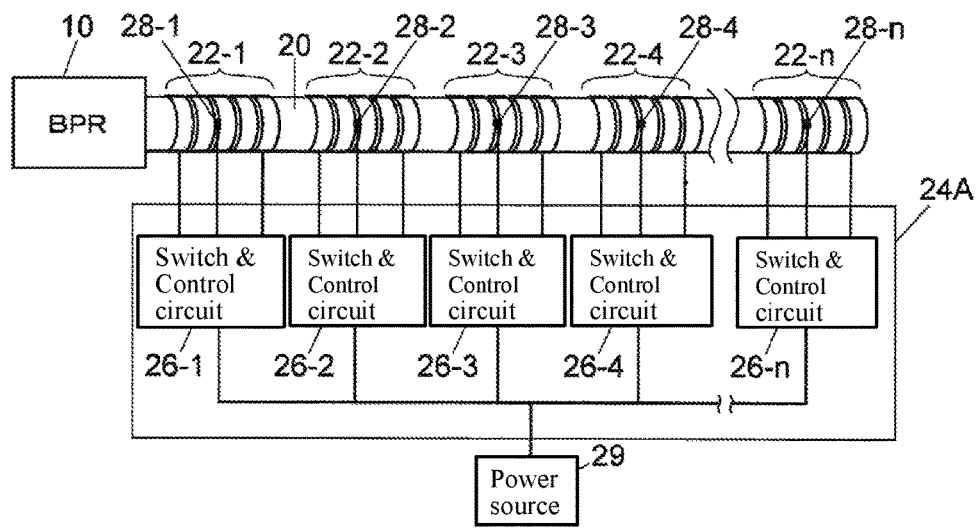
FIG. 6 is a block diagram showing a first embodiment in which heaters provided on a pipe and divided into a plurality of segments are separately controlled.
Figure 7:
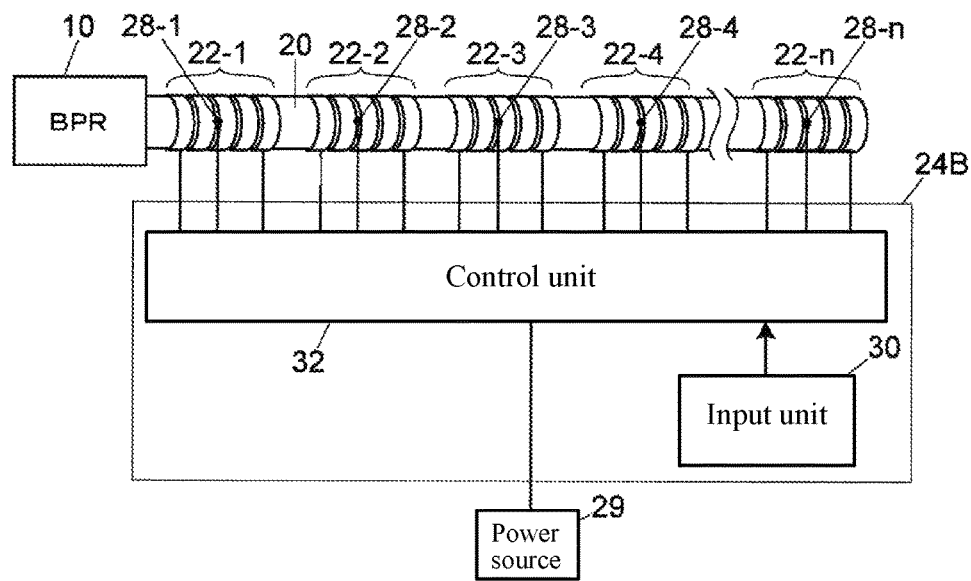
FIG. 7 is a block diagram showing a second embodiment in which heaters provided on a pipe and divided into a plurality of segments are separately controlled.
Figure 8:
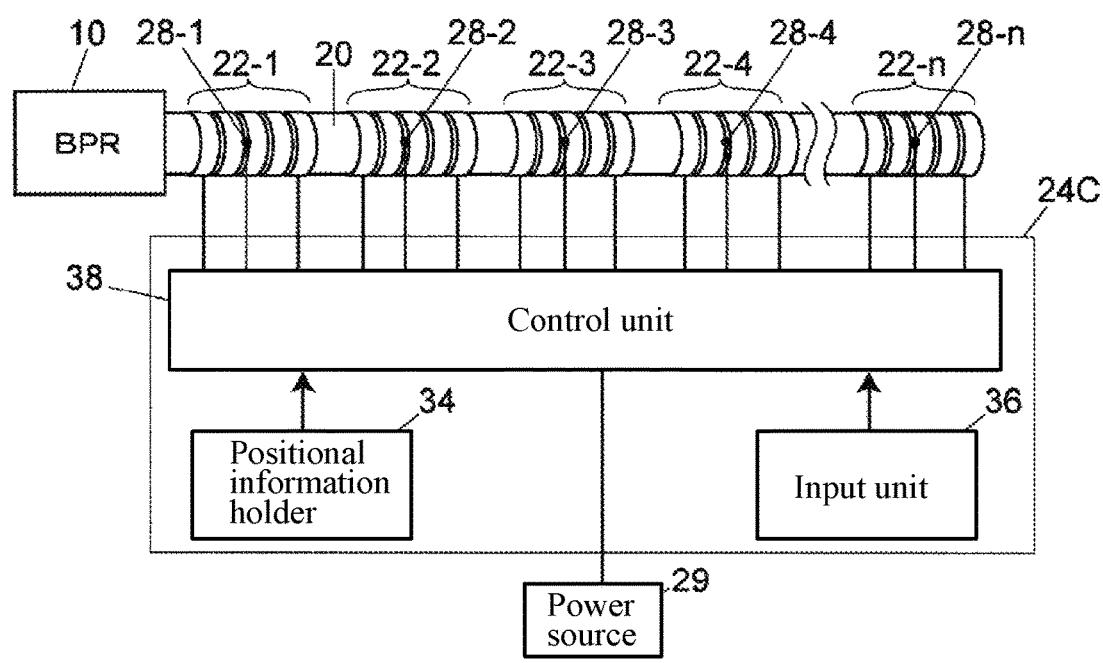
FIG. 8 is a block diagram showing a third embodiment in which heaters provided on a pipe and divided into a plurality of segments are separately controlled.

Examples are shown in FIGS. 6 to 8 in which heaters 22-1 to 22-$n$ divided into a plurality of segments and provided on the pipe 20 to heat the pipe 20 connected to the outlet side of the back pressure regulator 10 are controlled to be energized by being individually selected. Power for heating is supplied from a power source 29 to the selected heater 22-1 to 22-$n$.

In the embodiment of FIG. 6, the power supply controller 24A includes a switches and control circuits 26-1 to 26-$n$ for setting energization for each heater 22-1 to 22-$n$. Among heaters 22-1 to 22-$n$, heaters to be energized are selected by the switches and control circuits 26-1 to 26-$n$. The selection can be performed by manually operating the switches of the switches and control circuits 26-1 to 26-$n$.

Further, the switch and control circuits 26-1 to 26-$n$ are configured to set the current values of the heaters 22-1 to 22-$n$ to be energized. Therefore, as an example, temperature sensors 28-1 to 28-$n$ such as thermistors are provided to the pipe portions provided with heaters 22-1 to 22-$n$, and the switches and control circuits 26-1 to 26-$n$ feedback-control the energization to the heaters based on the detection signal from the temperature sensors corresponding to the heaters to be energized. Although the heater is not limited to a film heater, in cases where it is a film heater, since temperature can be detected by its resistance value, it is possible to perform feedback control of energization to the heater based on the resistance value of the film heater.

In the embodiment of FIG. 7, heaters to be energized among the heaters 22-1 to 22-$n$ are set from an input unit. Therefore, in this embodiment, the power supply controller 24B includes an input unit 30 for inputting information on energization for each heater 22-1 to 22-$n$ for designating which of the heater 22-1 to 22-$n$ is a heater to be energized and a control unit 32 for setting energization for each heater 22-1 to 22-$n$ based on the input information from the input unit 30. For each heater 22-1 to 22-$n$, it is set whether or not energization is performed, and for heaters to be energized, its current value is feedback-controlled as described with reference to the embodiment of FIG. 6.

In the embodiment shown in FIG. 8, it is configured such that parameters including the inner diameter of the pipe 20 and the liquefied carbon dioxide flow rate in the mobile phase are input and energization to heaters corresponding to the parameters can be automatically set. Therefore, in this embodiment, the power supply controller 24C is equipped with a positional information holder 34 that holds positional information indicating the freezing portion of the pipe for a plurality of parameters including the pipe inner diameter and the liquefied carbon dioxide flow rate in the mobile phase, an input unit 36 for inputting parameters for operating a supercritical fluid analysis unit, and a control unit 38 for selectively energizing heaters for preventing freezing of the pipe 20 among the heaters 22-1 to 22-$n$ based on the parameters input from the input unit 36 and the positional information retained in the positional information holder 34.

The plurality of parameters held in the positional information holder 34 means plural sets of parameters, each set of parameters including the inner diameter of the pipe 20 and the liquefied carbon dioxide flow rate in the mobile phase. The positional information indicates which of one or a plurality of heaters 22-1 to 22-$n$ is energized with respect to the plurality of sets of parameters to effectively prevent freezing of the pipe. The parameters input from the input unit 36 are also a set of parameters including the inner diameter of the pipe 20 and the liquefied carbon dioxide flow rate in the mobile phase.

When the positional information holder 34 holds a set matching the input parameters, the control unit 38 selectively energizes heaters designated by the positional information corresponding to that parameter set. When the positional information holder 34 does not hold anything that matches the input set of parameters, the control unit 38 selectively energizes heaters specified by the positional information corresponding to the set of parameters closest to the input parameter set from among the parameter sets held in the positional information holder 34.

The control units 32 and 38 may be dedicated computers such as microcomputers or may be realized by a computer for controlling or data processing a supercritical fluid device provided with the heaters 22-1 to 22-$n$. The present invention is not limited to a supercritical fluid extractor and a preparative supercritical fluid chromatograph, but is effective for deriving a sample which is easy to denture with temperature to a detector at a temperature that does not cause degeneration even in a supercritical fluid device to which a detector such as an MS (mass spectrometer) is further connected after liquefied carbon dioxide has passed through a back pressure regulator and vaporized like an SFC-MS.

DESCRIPTION OF REFERENCE SYMBOLS

3: carbon dioxide pump
4: modifier pump
6: autosampler
8: column
9: detector
10: back pressure regulator
11: heating unit
12: fraction collector
20: pipe
22-1~22-n: film heater
26-1~26-n: switch and control circuit
28-1~28-n: temperature sensor
24A, 24B, 24C: power supply controller
30: input unit
32, 38: control unit
34: positional information holder
30, 36: input unit

The invention claimed is:

1. A supercritical fluid device comprises:
a supercritical fluid analysis unit, the supercritical fluid analysis unit including an analysis flow passage equipped with a separation/extraction unit configured to separate or extract a sample component, a fluid feeder equipped with a pump and configured to supply a mobile phase which becomes a supercritical fluid to the analysis flow passage arranged on an upstream side of the separation/extraction unit, and a back pressure regulator arranged on a downstream side of the separation/extraction unit with respect to a flow of the mobile phase and configured to create a pressurized state in which the mobile phase in the separation/extraction unit is kept in a supercritical fluid state;
a pipe having one end connected to an outlet side of the back pressure regulator and the other end opened to atmosphere;
a heating unit equipped with a plurality of electrically independent heaters arranged on mutually different portions of the pipe along the pipe; and
a power supply controller connected to the heaters and configured to supply heating power source to one or a plurality of heaters selected from among the plurality of heaters but to not supply heating power to the other heaters,
wherein the power supply controller comprises:
a positional information holder that holds positional information indicating a freezing portion of the pipe for a plurality of parameters of the supercritical fluid analysis unit including an inner diameter of the pipe and a flow rate of liquefied carbon dioxide in the mobile phase,
input circuitry configured to input a parameter during an operation of the supercritical fluid device, and
a control circuit configured to selectively supply power to a heater for preventing freezing of the pipe among the heaters based on the parameter input from the input circuitry and positional information held in the positional information holder.

2. The supercritical fluid device as recited in claim 1, wherein the power supply controller is equipped with a switch and a control circuit for controlling power supply to each heater.

3. The supercritical fluid device as recited in claim 2, wherein the switch and the control circuit are configured to set a current value.

4. The supercritical fluid device as recited in claim 1, wherein the heaters are arranged substantially over an entire length of the pipe.

5. The supercritical fluid device as recited in claim 1, wherein the heater is a film heater wound around the pipe.

* * * * *